United States Patent [19]

Kamiyama et al.

[11] 4,225,727

[45] Sep. 30, 1980

[54] PROCESS FOR THE PRODUCTION OF UNSATURATED ESTERS

[75] Inventors: Setsuo Kamiyama, Kawagoe; Kouji Shiozawa, Okegawa; Yoshiharu Okumura, Kawagoe; Katsumi Kaneko, Ooi, all of Japan

[73] Assignee: Toa Nenryo Kogyo Kabushiki Kaisha, Tokyo, Japan

[21] Appl. No.: 82,004

[22] Filed: Oct. 5, 1979

[51] Int. Cl.³ ............................................. C07C 67/055
[52] U.S. Cl. .............................. 560/244; 260/410.6; 560/1; 560/112
[58] Field of Search ................ 560/244, 112, 1; 260/410.6

[56] References Cited

U.S. PATENT DOCUMENTS

| | | | |
|---|---|---|---|
| 3,671,577 | 6/1972 | Ono | 560/244 |
| 3,755,423 | 8/1973 | Onoda | 560/244 |
| 3,922,300 | 11/1975 | Onoda | 560/244 |
| 4,075,413 | 2/1978 | Tanabe | 560/244 |
| 4,121,039 | 10/1978 | Parthasarathy | 560/244 |

OTHER PUBLICATIONS

Derwent Abs. of Belg. Pat. 832,254.
Derwent Abs. of Jap. Pat. 52-18,162.
Derwent Abs. of Jap. Pat. 47-39004.
Derwent Abs. of Jap. Pat. 47-39006.
Derwent Abs. of Jap. Pat. 47-31919.
Derwent Abs. of Jap. Pat. 51-149220.
Derwent Abs. of Jap. Pat. 50-1095.
Derwent Abs. of Jap. Pat. 50-51094.
Derwent Abs. of Jap. Pat. 52-28495.

*Primary Examiner*—Natalie Trousof
*Assistant Examiner*—Michael Shippen
*Attorney, Agent, or Firm*—Rebecca Yablonsky

[57] ABSTRACT

The invention relates to a process for the production of an unsaturated glycol diester by the reaction of a conjugated diene compound, a carboxylic acid and molecular oxygen in the presence of a solid catalyst. For example, 1,4-diacetoxy-2-butene is prepared at high conversion and high selectivity by reacting butadiene, molecular oxygen and acetic acid in the presence of a solid catalyst containing palladium, tellurium and at least one element selected from the group consisting of tin, germanium and lead. The product is an intermediate for the preparation of 1,4-butanediol.

8 Claims, No Drawings

PROCESS FOR THE PRODUCTION OF UNSATURATED ESTERS

BACKGROUND OF THE INVENTION

1. Field of the Invention

This invention relates to a process for the production of an unsaturated glycol diester from a conjugated diene compound and, more particularly, it is concerned with a process for the production of an unsaturated glycol diester comprising reacting a conjugated diene compound, carboxylic acid and molecular oxygen in the presence of a solid catalyst.

2. Description of the Prior Art

The above reaction is known. In particular, when the carboxylic acid is acetic acid, the reaction may be depicted illustratively as follows:

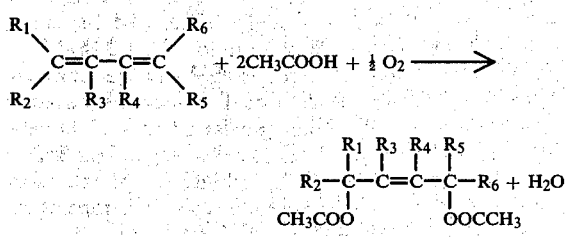

wherein $R_1$ to $R_6$ are individually a hydrogen atom or a hydrocarbon group, preferably an alkyl group having 1 to 6 carbon atoms.

Unsaturated glycol diesters are very useful as raw materials for various chemical processes. Above all, 1,4-glycol diesters are particularly important as raw materials for preparing organic solvents such as tetrahydrofuran or synthetic resins such as polyurethane resins and polybutylene terephthalate and various proposals have hitherto been made for the production of the same.

In the process for the production of 1,4-glycol diesters, it has been considered desirable to use a palladium type catalyst. For example, in U.S. Pat. No. 3,755,423, 1,4-diacetoxy-2-butene is obtained with high conversion as well as high selectivity by reacting 1,3-butadiene with acetic acid using a solid catalyst containing palladium, at least one of antimony and bismuth and at least one of tellurium and selenium.

Even in the case of using this catalyst, however, the catalyst efficiency, in particular, the palladium efficiency (Mols of diacetoxybutene formed/Catalyst palladium atom hour) is quite low and unsatisfactory in comparison with the catalyst for the synthesis of vinyl acetate by ethylene process which has already been practiced on a commericial scale as a reaction of this type.

A representative patent of Mitsubishi Chemical Company, Japanese Patent Public Disclosure No. 11812/74, reported that the addition of a small amount of tellurium to the Pd/C catalyst results in a dramatic increase in activity for acetoxylation with high selectivity to 1,4-diacetoxy-2-butene (92%).

On the other hand, BASF's patent, Japanese Patent Public Disclosure No. 63119/76, reported that carbon-supported palladium telluride (Pd4Te/C) catalyst, which is prepared with a controlled ratio of Pd to Te and gave no diffraction line of metallic palladium in X-ray analysis, shows good activity for acetoxylation.

Both palladium efficiency for diacetoxybutenes (DAB) formation over Pd-Te/C (8.4 mol-DAB/g-atom Pd/Hr) and Pd4Te/C catalyst, (6.4), however, remained at an insufficient level as a commercial catalyst.

Other patents in this area include U.S. Pat. Nos. 3,671,577; 3,922,300; 4,075,413; 4,121,039 and the following Japanese Patent Public Disclosure Nos.:

47-39003
47-39004
47-39006
47-31919
49-101322
49-11813
50-51094
50-51095
51-149220
52-28495

Thus the prior art has taught that in the preparation of solvents such as 1,4-butanediol from butadiene, the key to the process is the initial acetoxylation step wherein a carbon supported Pd-Te catalyst system is used.

SUMMARY OF THE INVENTION

Applicants have made studies on a catalyst system capable of producing unsaturated esters, for example, 1,4-diacetoxy-2-butene, with a higher catalytic efficiency suitable for commercial scale operation for the purpose of solving the above described problems and have found that unsaturated esters can be obtained with a high catalytic efficiency and a higher selectivity by the use of a solid catalyst containing (a) palladium, (b) tellurium and (c) at least one of tin, germanium and lead. The present invention is based on this finding.

That is to say, the present invention provides a process for the production of an unsaturated glycol diester, which comprises reacting a conjugated diene compound, a carboxylic acid and molecular oxygen in the presence of a solid catalyst containing (a) palladium, (b) tellurium and (c) at least one of Group IV elements of the Periodic Table selected from the group consisting of tin, germanium and lead. These are the heavy metals of Group IVA.

DETAILED DESCRIPTION

The metallic components used for the preparation of the catalyst used in the process of the present invention come from the following compounds:

For palladium, there may be used palladium chloride, palladium nitrate, palladium sulfate, palladium hydroxide, palladium oxide and the like.

For tellurium, there may be used tellurium dioxide, tellurium trioxide, tellurium dichloride, tellurium tetrachloride, tellurium tetraoxide, telluric acid and the like.

For the third components, i.e., tin, germanium and lead, there may be used their oxides, chlorides, nitrates, carboxylates and the like, for example, stannous chloride, tin nitrates, tin oxides, germanium tetrachloride, germanium oxides, germanium hydroxides, lead nitrate, lead chloride, lead acetate, etc.

The support for the catalytic components is not particularly limited, but, for example, active carbon, silica gel, silica-alumina, alumina, pumice, kieselguhr and silicon carbide may be used. In particular, active carbon is preferred. The support may be used as it is commercially sold or after it is subjected to a heat treatment or an acid treatment with nitric acid or hydrochloric acid.

The method of supporting the catalytic components may suitably be chosen from the ordinary methods of preparing supported catalysts. In the case of supporting by impregnation, for example, catalytic components are dissolved in a suitable solvent such as water, aqueous acidic solution of hydrochloric acid or nitric acid, aqueous alkaline solution or organic solvent, in which a support is immersed. Catalytic components may simultaneously or successively be dissolved in a solvent followed by impregnation.

In the present invention, the amounts of the catalytic components supported are preferably adjusted as follows. The amount of palladium supported is preferably 0.1 to 10.0% by weight and even if less than 0.1% by weight or more than 10.0% by weight, the reaction can proceed. The amount of tellurium is preferably 0.01 to 5.0% by weight, more preferably 0.1 to 3.0% by weight. The amount of at least one of tin, germanium and lead is preferably 0.01 to 10.0% by weight, more preferably 0.1 to 3.0% by weight of the total catalyst.

The atomic ratio of tellurium and at least one of tin, germanium and lead to palladium in the catalyst is preferably 0.05 to 10 gram atoms to 1 gram atom of palladium, more preferably 0.1 to 5 gram atoms of tellurium and 0.1 to 2 gram atoms of at least one of tin, germanium and lead to 1 gram atom of palladium.

The support having the catalytic components is then subjected to removal of the solvent and to reduction in a hydrogen stream or in a gaseous stream containing an organic compound capable of reducing, in general, at a reducing temperature of 150° to 500° C., preferably 200° to 400° C., for 2 to 10 hours, thus producing a catalyst.

Examples of the conjugated diene compound used as a raw material in the process of the present invention are 1,3-butadiene and hydrocarbon substituted derivatives thereof such as isoprene, 1,3-pentadiene, 2,3-dimethyl-1,3-butadiene, 1,3-hexadiene, 2,4-hexadiene, 1,3-octadiene and 4-phenyl-1,3-butadiene, and cyclic conjugated diene compounds such as cyclopentadiene, 1,3-cyclohexadiene and 1,3-cyclooctadiene. Above all, 1,3-butadiene is preferred. It is not always required that the conjugated diene compound be pure, but nitrogen, carbon dioxide or a lower saturated hydrocarbon such as methane, ethane, propane or butane may be admixed therewith.

The carboxylic acid as another raw material in the process of the present invention may be selected from saturated or unsaturated aliphatic carboxylic acids and aromatic carboxylic acids having 2 to 20 carbon atoms. Lower aliphatic mono carboxylic acids containing 2 to 4 carbon atoms such as acetic acid, propionic acid and butyric acid are preferably used and, in particular, acetic acid is more preferable.

The molecular oxygen used in the process of the present invention does not have to be pure but may be diluted with an inert gas such as nitrogen or carbon dioxide, and of course may be air.

The reaction conditions employed in the process of the present invention are as follows: The reaction may be carried out batch-wise or continuously in liquid phase using a fixed bed or fluidized bed. The reaction temperature, pressure and feed quantities of a conjugated diene compound, carboxylic acid and molecular oxygen are not particularly limited but preferably the reaction temperature ranges from 40° C. to 180° C., the pressure ranges from atmospheric to 100 Kg/cm$^2$ and the molar ratio of conjugated diene compound/carboxylic acid/molecular oxygen is in the range of 1/0.5–10.0/0.1–5.0.

The following examples are provided in order to illustrate the present invention in detail without limiting the same.

EXAMPLE 1

0.1750 g of palladium chloride and 0.0250 g of tellurium dioxide were dissolved in 40 ml of 6N hydrochloric acid, to which a methanol solution of 0.2214 g of stannous chloride ($SnCl_2 \cdot 2H_2O$) was added, and 10 g of active carbon of 24 to 42 mesh, previously heated and refluxed with 15% by weight nitric acid for 6 hours, was immersed in the resulting solution at room temperature for 24 hours. After the immersion, the mixture was then evaporated gradually to dryness on a warm water bath, dried at 150° C. for 3 hours in a nitrogen stream in a tube and reduced with nitrogen saturated with methanol at room temperature at 200° C. for 3 hours and at 400° C. for 2 hours, thus obtaining a catalyst containing 1.05% by weight of palladium, 0.20% by weight of tellurium and 1.16% by weight of tin and having a palladium/tellurium/tin atomic ratio of 1.0/0.16/1.0.

4 g of the catalyst prepared in this way was charged to a reaction tube of stainless steel with an inner diameter of 18 mm, through which glacial acetic acid, butadiene and oxygen were passed at a rate of 12.5 ml/hr, 60 mmol/hr and 40 mmol/hr respectively, and the reaction was carried out continuously at a reaction temperature of 80° C.

Analysis of the product after passage of 5 hours from the start of the reaction gave the space time yield (g/catalyst 1 hr), palladium efficiency (mol/palladium atom.hr) and 1,4-isomer selectivity (%) shown in Table 1.

EXAMPLES 2 AND 3

The preparation of a catalyst and the reaction using the same were carried out in a manner analogous to Example 1 except that 0.2124 g of germanium tetrachloride or 0.3271 g of lead nitrate was added in place of the stannous chloride of Example 1, thus obtaining the results shown in Table 1. In Example 2, a solution of germanium tetrachloride in absolute alcohol was added and in Example 3, a solution of lead nitrate in hydrochloric acid was added.

COMPARATIVE EXAMPLES 1 AND 2

The preparation of a catalyst and the reaction using the same were carried out in a manner analogous to Example 1 except that a combination of palladium chloride with tellurium dioxide or palladium chloride with stannous chloride was used to obtain the results shown Table 1.

COMPARATIVE EXAMPLE 3

The preparation of a catalyst and the reaction using the same were carried out in a manner analogous to Example 1 except that a combination of 0.0250 g of tellurium dioxide and 0.2214 g of stannous chloride only was used to obtain the results shown in Table 1.

TABLE 1

|  |  | Supported Components | Space Time Yield (g/1-cat . hr) | Palladium Efficiency (mol/ atom . hr) | 1,4-diacetoxy-2-butene Selectivity (%) |
|---|---|---|---|---|---|
| Example | 1 | Pd-Te-Sn | 126.0 | 17.9 | 91.9 |
|  | 2 | Pd-Te-Ge | 112.8 | 16.0 | 91.7 |
|  | 3 | Pd-Te-Pb | 101.1 | 14.4 | 92.0 |

TABLE 1-continued

| | Supported Components | Space Time Yield (g/l-cat . hr) | Palladium Efficiency (mol/atom . hr) | 1,4-diacetoxy-2-butene Selectivity (%) |
|---|---|---|---|---|
| Comparative Example | 1 Pd-Te | 69.3 | 9.1 | 92.3 |
| | 2 Pd-Sn | 0.9 | 0.1 | — |
| | 3 Te-Sn | 0.4 | — | — |

COMPARATIVE EXAMPLES 4 to 10

The preparation of a catalyst and the reaction using the same were carried out in a manner analogous to Example 1 except that each of the following metal salts was added in such a manner that the atomic ratio of the supported metal to palladium was 1.0 in place of the stannous chloride of Example 1, thus obtaining the results shown in Table 2.

Each of cuprous chloride, nickel nitrate, ferric nitrate, ammonium molybdenate, potassium acetate, antimony trichloride and bismuth nitrate was dissolved in 6N hydrochloric acid with palladium chloride and tellurium dioxide.

TABLE 2

| | Supported Components | Space Time Yield (g/l-cat . hr) | Palladium Efficiency (mol/atom . hr) | 1,4-diacetoxy-2-butene Selectivity (%) |
|---|---|---|---|---|
| Comparative Example | 4 Pd-Te-Cu | 51.9 | 7.4 | 91.4 |
| | 5 Pd-Te-Ni | 49.4 | 7.1 | 91.8 |
| | 6 Pd-Te-Fe | 45.8 | 6.5 | 90.1 |
| | 7 Pd-Te-Mo | 59.1 | 8.0 | 90.0 |
| | 8 Pd-Te-K | 42.7 | 6.0 | 92.4 |
| | 9 Pd-Te-Sb | 78.5 | 10.3 | 92.2 |
| | 10 Pd-Te-Bi | 72.7 | 9.6 | 91.9 |

EXAMPLE 4

The catalyst of palladium-tellurium-tin/active carbon prepared in Example 1 was charged to a pressure-resisting reaction tube of stainless steel with an inner diameter of 14mm, through which 6.7 ml/hr of glacial acetic acid, 4.0 ml/hr of liquid 1,3-butadiene and 470 N ml/min of nitrogen gas containing 3 mol % of oxygen were passed, and the reaction was continuously carried out in liquid phase at a reaction temperature of 100° C. under a pressure of 40 Kg/cm$^2$ to obtain the results shown in Table 3.

COMPARATIVE EXAMPLE 11

The reaction was carried out in a manner analogous to Example 4 except that the catalyst of palladium-tellurium/active carbon prepared in Comparative Example 1 was used to obtain the results shown in Table 3.

TABLE 3

| | Supported Components | Reaction Period (hr) | Space Time Yield (g/1-cat . hr) | Palladium Efficiency (mol/atom . hr) | 1,4-diacetoxy-2-butene Selectivity (%) |
|---|---|---|---|---|---|
| Example 4 | Pd-Te-Sn | 10 | 210.3 | 29.9 | 91.6 |
| | | 100 | 189.8 | 27.0 | 91.7 |
| Comparative Example 11 | Pd-Te | 10 | 112.2 | 15.7 | 91.8 |
| | | 100 | 69.1 | 9.1 | 92.1 |

EXAMPLES 5 to 8

The reaction was carried out in a manner analogous to Example 1 and each of the Pd-Te-Sn catalysts was prepared similarly except that stannous chloride was added to give an Sn/Pd atomic ratio ranging from 0.1 to 2.0, thus obtaining the results shown in Table 4.

TABLE 4

| | Sn/Pd | Space Time Yield (g/1-cat . hr) | Palladium Efficiency (mol/atom . hr) | 1,4-diacetoxy-2-butene Selectivity (%) |
|---|---|---|---|---|
| Example 5 | 0.1 | 89.8 | 12.8 | 92.2 |
| 6 | 0.5 | 137.1 | 19.5 | 92.0 |
| 7 | 1.0 | 126.0 | 17.9 | 91.9 |
| 8 | 2.0 | 79.2 | 11.3 | 91.8 |

EXAMPLES 9-10 AND COMPARATIVE EXAMPLES 12-14

Comparison with BASF and Mitsubishi Chemical Co. processes in catalyst performance is summarized in Table 5. The catalysts of Examples 9 and 10 were prepared in a manner analogous to Example 1.

Both Examples 9 and 10 gave a Pd efficiency superior to Comparative Examples 12-14. The Pd-Te-Sn/C catalyst in Example 10 gave excellent palladium efficiency (32.7 mol-DAB/g-atom Pd/hr) which is substantially equivalent to the commercial one of vinyl acetate synthesis from ethylene over a Pd catalyst. Pd efficiency for commercial vinyl acetate synthesis is estimated to be about 50. This value corresponds to about 25 pd efficiency for diacetoxylation.

TABLE 5

Comparison with BASF and Mitsubishi Chemical Co. Processes in Catalyst Performance

| | | Conditions | | | | | Palladium Efficiency | Selectivity | |
|---|---|---|---|---|---|---|---|---|---|
| | | Temp. | Press. | Feed molar ratio | | | (mol-DAB/g . | to 1,4-DAB | |
| Example No. | Catalyst | °C. | atm. | C$_4$= | O$_2$ | AcOH | atom-Pd/hr) | (%) | Note |
| Comparative Example 12 (BASF) | Pd4Te/C Pd 3.19 wt % Te 0.96 wt % Te/Pd 0.25 | 80 | 7 | 1 | 0.87 | 8.68 | 6.4 | 97.5 | According to Jap. Pat. Public Discl. No. 63119/76 |
| Comparative Example 13 | Pd-Te/C Pd 2.13 wt % | 80 | Atm. | 1 | 0.67 | 7.28 | 8.4 | 92.2 | According to Jap. Pat. Public Discl. No. |

TABLE 5-continued
Comparison with BASF and Mitsubishi Chemical Co. Processes in Catalyst Performance

| Example No. | Catalyst | Conditions | | | | | Palladium Efficiency (mol-DAB/g. atom-Pd/hr) | Selectivity to 1,4-DAB (%) | Note |
| --- | --- | --- | --- | --- | --- | --- | --- | --- | --- |
| | | Temp. °C. | Press. atm. | Feed molar ratio | | | | | |
| | | | | $C_4^=$ | $O_2$ | AcOH | | | |
| (Mitsubishi Chemical Co.) | Te 0.38 wt. % Te/Pd 0.15 | | | | | | | | 11812/74 |
| Comparative Example 14 | Pd-Te/C Pd. 1.05 wt % Te 0.20 wt % Te/Pd 0.16 | 80 | Atm. | 1 | 0.67 | 7.28 | 9.1 | 92.3 | Repeat experiment for Jap. Pat. Public Discl. No. 11812/74 |
| Example 9 | Pd-Te-Sn/C Pd 1.05 wt % Te 0.20 wt % Sn 1.15 wt % Te/Pd 0.16 Sn/Pd 1.00 | 80 | Atm. | 1 | 0.67 | 7.28 | 17.9 | 91.9 | According to this invention |
| Example 10 | Pd-Te-Sn/C Pd 0.77 wt % Te 0.31 wt % Sn 0.68 wt % Te/Pd 0.34 Sn/Pd 0.80 | 80 | Atm. | 1 | 0.67 | 7.28 | 32.7 | 91.0 | According to this invention |

What is claimed is:

1. In a process for the production of an unsaturated ester which comprises reacting a conjugated diene compound, a carboxylic acid and molecular oxygen in the presence of a solid catalyst containing (a) palladium and (b) tellurium, the improvement which comprises including in the catalyst (c) at least one of Group IV elements of the Periodic Table selected from the group consisting of tin, germanium and lead.

2. A process according to claum 1 in which the conjugated diene compound is butadiene which may be substituted by alkyl or phenyl groups and the carboxylic acid may be aliphatic, alicyclic or aromatic.

3. A process according to claim 2 in which the butadiene is substituted by at least one methyl group.

4. A process according to claim 2 or 3 in which the carboxylic acid is a lower aliphatic monocarboxylic acid containing 2–4 carbon atoms.

5. A process according to claim 1 in which the reactants are butadiene, acetic acid and molecular oxygen and 1,4-diacetoxy-2-butene is obtained.

6. A process according to claim 1 or claim 5 in which the reaction temperature is in the range of 40° to 180° C., the reaction pressure is in the range of atmospheric to 100 Kg/cm² and the molar ratio of conjugated diene compound/carboxylic acid/molecular oxygen is in the range of 1/05.–10.0/0.1–5.0.

7. A process according to claim 1 or claim 5 in which the atomic ratio of tellurium and at least one of the metals tin, germanium and lead, to palladium, in the catalyst is 0.05 to 10 gram atoms to 1 gram atom of palladium.

8. A process according to claim 1 or claim 5 in which the atomic ratio of tellurium to at least one of the metals tin, germanium and lead, to palladium is 0.1–5/0.1–2/1.

* * * * *